United States Patent [19]

Takeda et al.

[11] Patent Number: 4,618,631

[45] Date of Patent: Oct. 21, 1986

[54] PRODUCTION PROCESS FOR HIGHLY WATER ABSORBABLE POLYMER

[75] Inventors: Hisao Takeda, Zama; Yasunori Taniguchi, Samukawamachi, both of Japan

[73] Assignee: American Colloid Company, Skokie, Ill.

[21] Appl. No.: 836,103

[22] Filed: Mar. 4, 1986

Related U.S. Application Data

[62] Division of Ser. No. 710,702, Mar. 11, 1985, which is a division of Ser. No. 460,037, Jan. 21, 1983, Pat. No. 4,525,527.

[30] Foreign Application Priority Data

| | | | |
|---|---|---|---|
| Jan. 25, 1982 | [JP] | Japan | 57-8983 |
| Mar. 9, 1982 | [JP] | Japan | 57-035913 |
| Mar. 9, 1982 | [JP] | Japan | 57-035914 |

[51] Int. Cl.$^4$ .................................... C08J 9/02
[52] U.S. Cl. ........................ 521/109.1; 521/134; 521/139; 521/905
[58] Field of Search ............... 521/109.1, 134, 139, 521/905; 524/555, 827, 829, 831

[56] References Cited

U.S. PATENT DOCUMENTS 4,394,457  7/1983  Ogasa .................................. 521/139

Primary Examiner—Harry Wong, Jr.
Attorney, Agent, or Firm—Mason, Kolehmainen, Rathburn & Wyss

[57] ABSTRACT

Disclosed is a process for preparing water absorbing, cross-linked acrylate resins by aqueous polymerization of (A) acrylic acid neutarlized 70 to 100 mole percent for example with ammonia, and/or caustic alkali and/or an amine; with (B) acrylamide in a mole ratio of 70 to 100 mole percent (A) to 30:0 mole percent (B); and (C) a water miscible or a water soluble polyvinyl monomer in an amount of 0.001 to 0.3 weight percent based on the total weight of (A) and (B). In accordance with one embodiment of the invention, the concentration of monomers (A) plus (B) should be at least 70 percent by weight of the polymerization mixture of (A) plus (B) plus (C) to achieve a substantially dry polymer (less than 15 weight percent water) when polymerization is completed by utilizing the exothermic heat of polymerization and cross-linking to drive off water without the need for additional heating to obtain a dry solid. The addition of polystyrene and/or methylcellulose substantially increases the water absorbing capacity of these polymers.

3 Claims, No Drawings

PRODUCTION PROCESS FOR HIGHLY WATER ABSORBABLE POLYMER

CROSS REFERENCE TO RELATED APPLICATION

This application is a division of copending application Ser. No. 710,702 filed Mar. 11, 1985 which is a division of application Ser. No. 460,037 filed Jan. 21, 1983, now U.S. Pat. No. 4,525,527 issued June 25, 1985.

FIELD OF THE INVENTION

The present invention relates to a method of manufacturing polyacrylate resins having improved water absorbing properties and more particularly to an improved process of preparing cross-linked polymers of acrylic acid, acrylamide and polyvinyl monomers.

BACKGROUND OF THE INVENTION

Water absorbing resins have found wide use in sanitary goods, hygenic goods, water retaining agents, dehydrating agents, sludge coagulants, thickening agents, condensation preventing agents and release control agents for various chemicals. Water absorbing resins heretofore known include hydrolysis products of starch-acrylonitrile graft polymers, carboxymethylcellulose, cross-linked polyacrylate products and other resins such as polyvinyl alcohol, polyethylene oxide and polyacrylonitrile resins. Of these water absorbing resins, the hydrolysis products of starch and acrylonitrile graft polymers have comparatively high ability to absorb water but require a cumbersome process for production and have the drawbacks of low heat resistance and decaying or decomposing easily due to the presence of starch.

One of the processes for polymerizing acrylic acid and acrylates is aqueous solution polymerization. The polymer obtained by this process is soluble in water and, therefore, is cross-linked to modify the polymer into a useful water absorbing resin. However, even if the modification is effected by reacting a cross-linking agent concurrently with or after aqueous solution polymerization, the resulting reaction product is in the form of a highly viscous aqueous solution or a gel containing absorbed water which is difficult to handle. Thus, the aqueous solution or gel must be dehydrated (dried) to obtain a water absorbing resin in the desired solid or powder form. It is nevertheless difficult to dry the reaction product efficiently by the usual rotary drum roller method or spray drying method because care must be taken to avoid excessive cross-linking which results from overheating during drying and insufficient drying results in reduced cross-linking density. Extreme difficulties are therefore encountered in preparing a product of a desired low water content and good water absorbing ability.

SUMMARY OF THE INVENTION

An object of the present invention is to provide a process for preparing a water absorbing cross-linked acrylate resin of low water content by aqueous solution polymerization without any additional dehydrating or drying step.

Another object of the present invention is to provide a process for preparing a cross-linked polyacrylate resin by co-polymerization of acrylic acid neutralized 70-90 mole percent, with acrylamide and a polyvinyl monomer in proportions of 0 to 30 mole percent acrylamide and 70-100 mole percent partially neutralized acrylic acid.

Another object of the present invention is to provide a process for producing a polyacrylate resin cross-linked with 50-200 parts per million, based on the weight of monomers, of a water miscible or water soluble polyvinyl cross-linking agent.

Still another object of the present invention is to provide a method of manufacturing a cross-linked polyacrylate resin polymerized in aqueous solution having a monomer concentration of at least 70 weight percent so that the heat of polymerization and cross-linking drives off the water to provide a dry (less than 15% by weight water), solid resin.

In brief, the present invention is directed to a process for preparing water absorbing, cross-linked acrylate resins by aqueous polymerization of (A) acrylic acid neutralized 70 to 100 mole percent for example with ammonia, and/or caustic alkali and/or an amine; with (B) acrylamide in a mole ratio of 70 to 100 mole percent (A) to 30:0 mole percent (B); and (C) a water miscible or a water soluble polyvinyl monomer in an amount of 0.001 to 0.3 weight percent based on the total weight of (A) and (B).

In accordance with one important embodiment of the present invention, the concentration of monomers (A) plus (B) should be at least 70 percent by weight of the polymerization mixture of (A) plus (B) plus (C) to achieve a substantially dry polymer (less than 15 weight percent water) when polymerization is completed by utilizing the exothermic heat of polymerization and cross-linking to drive off water without the need for additional heating to obtain a dry solid.

DETAILED DESCRIPTION OF THE INVENTION

In accordance with one embodiment of the present invention a cross-linked polyacrylate resin is prepared by aqueous solution polymerization while dehydrating or drying the reaction product during polymerization by utilizing the exothermic heat from the polymerization and cross-linking reactions for drying.

It has been found that acrylic acid neutralized in the range of 70 to 100 mole percent will polymerize rapidly with acrylamide and cross-link rapidly with a polyvinyl monomer cross-linking agent to drive away excess water leaving a solid water absorbing resin having a desired degree of polymerization as well as new and unexpected water absorbing capacity. One or more polymerization catalysts or initiators can be added to the aqueous monomer mixture to aid in polymerization.

Acrylic acid neutralized 70-100 mole percent is mixed with a water-miscible or water-soluble polyvinyl monomer in an aqueous solution at a temperature of about 20° to 100° C. The solution is subjected to a polymerization reaction and a cross-linking reaction by the addition of a polymerization initiator. The polymerization reaction proceeds sufficiently within a very short period of time and if the monomer concentration is at least 70 percent by weight of the aqueous monomer mixture, the heat or the polymerization and cross-linking reactions will evaporate water rapidly from the reaction system to form a dry solid (less than 15 percent by weight water) water absorbing resin without the need for any subsequent drying step. The solid can be easily pulverized into a powder suitable for any desired use.

Further, according to one embodiment of the invention, when the monomer concentration is at least 70 percent by weight of the polymerization mixture, the polymerization reaction and evaporation of water can be completed very rapidly, usually within several minutes, without external heating. The process can be practiced very efficiently with greatly reduced consumption of heat energy while achieving a desired degree of polymerization very suitable for a commercial operation.

According to the process of the invention, a hot, i.e. at least 25° C., aqueous solution is prepared first including acrylic acid neutralized 70 to 100 mole percent, acrylamide, a water-miscible or water-soluble polyvinyl monomer, and water. The aqueous solution can be prepared easily by placing (A) acrylic acid, and an amine, and/or a caustic alkali and/or ammonia for neutralizing the acid; (B) acrylamide; and (C) a polyvinyl monomer into water to form a mixed monomer solution. In accordance with one important embodiment of the present invention, the monomers comprise at least 70 percent by weight of the mixed solution to provide a self drying mixture upon polymerization and cross-linking. To dissolve the monomers thoroughly, the mixture can be heated to an elevated temperature up to the boiling point of water i.e. 100° C.

Others who have attempted aqueous polymerization of acrylic monomers have found that potassium neutralization of acrylic acid is the only way to obtain an acrylate polymer having sufficient water absorbing capacity and have found that potassium acrylate is necessary to achieve a polymerizable monomer mixture of sufficiently high concentration to achieve self drying. In accordance with the present invention, it has been found that by including acrylamide in the monomer mixture, the acrylic acid can be neutralized with a substantial number of neutralizing agents, such as ammonia or an amine, or any alkali metal compound in addition to potassium hydroxide, such as a sodium hydroxide, lithium hydroxide, cesium hydroxide, potassium carbonate or sodium carbonate without difficulty in preparing an aqueous solution of high concentration i.e. 70-90 weight percent. Further, tne resulting water absorbing resins have unexpectedly high water absorbing capacity. Addition of the neutralizing agent in molar excess will not cause any particular problem, but the excess does not participate in the polymerization reaction.

The polyvinyl monomer to be used in the invention should be miscible with or soluble in water so that the monomer will be uniformly dissolved or dispersed in the aqueous solution of the monomer mixture. Examples of such polyvinyl monomers include bisacrylamides such as N,N'-methylenebisacrylamide and N,N'-methylenebismethacrylamide; polyacrylic (or polymethacrylic) acid esters represented by the following formula (I); and diacrylamides represented by the following formula (II). Among these, especially preferably are N,N'-methylenebisacrylamide, N,N'-methylenebismethacrylamide and like bisacrylamides.

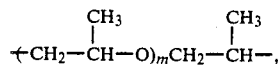

wherein X is ethylene, propylene, trimethylene, hexamethylene, 2-hydroxypropylene, $(CH_2CH_2O)_nCH_2CH_2-$ or

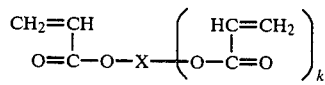

n and m are each an integer of from 5 to 40, and k is 1 or 2.

The compounds of the formula (I) are prepared by reacting polyols, such as ethylene glycol, propylene glycol, trimethylolpropane, 1,6-hexanediol, glycerin, pentaerythritol, polyethylene glycol and polypropylene glycol, with acrylic acid or methacrylic acid. Formula (II):

wherein l is 2 or 3.

The compounds of the formula (II) are obtained by reacting polyalkylenepolyamines, such as diethylenetriamine and triethylenetetramine, with acrylic acid.

The polyvinyl monomer is used in an amount of about 0.001 to 0.3 wt. %, preferably 0.005 to 0.1 wt. %, of the amount of acrylic monomers in the aqueous monomer mixture. If more than about 0.3 weight percent of the polyvinyl monomer is used, the resulting polymer will have exceedingly high strength when in the form of a gel on absorption of water and therefore exhibit impaired water absorbing ability, whereas if it is used in an amount below about 0.001 weight percent, a polymer sol will be obtained having low gel strength exhibiting reduced water absorbing ability.

The aqueous mixed monomer solution is heated and thereafter subjected to polymerization and cross-linking reactions with the addition of a polymerization initiator. Although the temperature of the aqueous mixed monomer solution is not particularly limited since the mixed monomer solution is initiated into polymerization by the addition of the initiator, the temperature is 25° to 850° C. and usually about 50° to about 85° C., preferably about 60° to about 75° C. Various polymerization initiators are usable which are known for use in preparing polyacrylates. Examples of useful initiators are redox initiators comprising a reducing agent, such as a sulfite or bisulfite of an alkali metal, ammonium sulfite or ammonium bisulfite, and an initiator, such as a persulfate of an alkali metal or ammonium persulfate, in combination with the reducing agent; azo initiators including azobisisobutyronitrile, 4-t-butylazo-4'-cyanovaleric acid, 4,4'-azobis(4-cyanovaleric acid) and 2,2'-azobis(2-amidinopropane)-hydrochloric acid salt; and the like These initiators can be used singly or in a suitable combination. Of these, especially preferable are a redox initiator composed of ammonium persulfate and sodium hydrogensulfite, and azo initiators such a azobisisobutyronitrile and 2,2'-azobis(2-amidinopropane)-hydrochloric acid. These initiators are advantageously used usually in the form of an aqueous solution but can be used as diluted with a suitable solvent. The initiator is used in a usual amount, i.e. in an amount, calculated as solids, of about 0.1 to about 10%, preferably about 0.5 to about 5%, of the combined weight of the monomers, namely acrylate (and free acrylic acid), acrylamide, and polyvinyl monomer. Depending on the amount and kind of the initiator, the initiator is usable together with isopropyl alcohol, alkylmercaptan or other chain transfer agents to control the molecular weight of the polyacrylate to be obtained.

By the addition of the polymerization initiator, the mixed monomer solution is subjected to polymerization with evaporation of water without heating the system from outside. More advantageously, the reaction is carried out by admixing a predetermined amount of the initiator or an aqueous solution thereof with the mixed monomer solution and causing the resulting mixture to flow down onto and spread over a traveling conveyor belt. The initiator can be added to the mixed monomer solution as it is poured onto the conveyor belt.

The polymerization proceeds rapidly after admixing the initiator with the mixed monomer solution and is completed within a short period of time, usually in about 30 seconds to about 10 minutes. The reaction is exothermic, so that the reaction system is rapidly heated to about 100 to about 130° C. by the heat of polymerization. Consequently, particularly where the monomer concentration in the mixed solution is at least 70 percent by weight, the water evaporates from the system rapidly to give a relatively dry, solid polymer of low water content without resorting to any external heating. The water content of the polymer, when reacted at high (at least 70 weight percent) monomer concentration, is usually up to about 15%, and generally about 8 to 12% by weight e.g. 10%. Subsequently, the dry solid polymer can be made into the desired powder easily by a usual method, for example by pulverization, without a drying step.

In accordance with another important feature of the present invention, polystyrene and/or methylcellulose can be added to the mixed monomer solution in an amount of 0.5 to about 10 percent based on the total weight of monomers in the mixed monomer solution to increase the porosity and water absorbing capacity of the polymers. It has been found, quite surprisingly, the polystyrene and methylcellulose will substantially increase the water absorbing capacity of the resin described herein. To achieve the full advantage of the present invention, the polystyrene and methylcellulose should be added in an average grain size of less than or equal to 5 micrometers. Examples 8-10 and 14-16 to follow show the surprising increase in water absorption with the addition of polystyrene or methylcellulose.

The powder thus obtained has outstanding water absorbing ability and is useful for sanitary goods, paper diaper, disposable diaper and like hygenic goods, agricultural or horticultural water retaining agents, industrial dehydrating agents, sludge coagulants, thickening agents, condensation preventing agents for building materials, release control agents for chemicals and various other applications.

The present invention will be described in greater detail with reference to the following examples.

EXAMPLE 1

281. gr. of acrylic acid and 11.9 gr. of acrylamide were dissolved in 179.1 gr. of distilled water and then 10.9 gr. of NaOH was added for 70 mole percent partial neutralization of acrylic acid; 0.003 gr. of N,N'-methylenebisacrylamide was then added as the polyvinyl monomer. In this case, 0.04 gr. of 2,2'-azobis(2-amidinopropane)-hydrochloride was added as the polymerization initiator and the initial temperature of the mixed monomer solution was 50° C.

EXAMPLE 2

48.1 gr. of acrylic acid and 11.9 gr. of acrylamide were dissolved in 159 gr. of distilled water and then 22.7 gr. of NaOH was added for partial neutralization of acrylic acid in an amount of 85 mole percent. 0.006 gr. of N,N'-methylenebisacrylamide was then added as the polyvinyl monomer. In addition, 0.048 gr. of ammonium persulfate and 0.048 gr. of sodium hydrogen-sulfite were added as the polymerization initiators. In this case, the initial temperature of the mixed monomer solution was 40° C.

EXAMPLE 3

90.1 gr. of acrylic acid and 9.9 gr. of acrylamide were dissolved in 118.8 gr. of distilled water and 52.6 gr. of KOH was added for 75 mole percent partial neutralization of acrylic acid. 0.018 gr. of N,N'-methylenebisacrylamide was added as the polyvinyl monomer, and 0.08 gr. of ammonium persulfate and 0.08 gr. of sodium hydrogen-sulfite were added as the polymerization initiators. The initial temperature of the mixed monomer solution was 30° C.

EXAMPLE 4

48.1 gr. of acrylic acid and 11.9 gr. of acrylamide were dissolved in 252.1 gr. of distilled water and 27.4 gr. of aqueous ammonia was added for 70 mole percent partial neutralization of acrylic acid. In this case, the concentration of the ammonia is 29 weight percent. In addition, 0.006 gr. of N,N'-methylenebisacrylamide was added as the polyvinyl monomer. The polymerization was performed with the addition of 0.04 gr. of ammonium persulfate and 0.048 gr. of sodium hydrogen-sulfite for initiation. In this case, the initial temperature of the mixed monomer solution was 30° C.

EXAMPLE 5

52.7 gr. of acrylic acid and 17.3 gr. of acrylamide were dissolved in 25 gr. of distilled water and they were partially neutralized 80 mole percent with the addition of 32.8 gr. of KOH. 0.007 gr. of N,N'-methylenebisacrylamide was added as to the polyvinyl monomer. For the polymerization catalyst 0.7 gr. of 2,2'-azobisisobutyronitrile dissolved in 10 cc. of acetone was added. This solution was kept at 80° C. in a TEFLON coated, glass fiber reaction chamber until completion of polymerization and cross-linking reactions yielding a white, solid resin.

EXAMPLE 6

17.3 gr. of acrylamide was dissolved in 52.7 gr. of acrylic acid and partial (70 mole percent) neutralization of acrylic acid was accomplished by the addition of 30 gr. of aqueous ammonia having a concentration of 29 weight percent. In this case, for the polyvinyl monomer, 0.007 gr. of N,N'-methylenebisacrylamide was added and, as the catalyst, 0.7 gr. of 2,2'-azobis(2-amidinopropane)-hydrochloride dissolved in 8 gr. of distilled water was added. The polymerization was started at 80° C. yielding a white, solid resin.

EXAMPLE 7

21 kg. of acrylic acid and 7 kg. of acrylamide were dissolved in 9.5 kg. of distilled water and the acrylic acid was partially neutralized with 12 kg. of KOH. 0.036 kg. of methylenebisacrylamide as a polyvinyl monomer was added to provide an aqueous mixed monomer solution. The mixed monomer solution was mixed with 0.28 kg. of 2,2'-azobisisobutyronitrile, dissolved in 2 kg. of acetone as a polymerization initiator. This mixture at a temperature of 60° C. was transferred on an endless belt (600-700 mm. in width, and 7 m. in length) at a thickness of about 1 cm. The polymerization was initiated promptly on the belt resulting in a white, solid resin.

EXAMPLE 8

The polymers of Examples 1-4, were dehydrated with acetone, dried and pulverized into powders. The polymers of Examples 5-7, were pulverized without any drying into highly water absorbable powders. The products of Examples 1-7, were compared to commercial prior art products. The testing method was as follows:

1 gr. of sample was added to 1 liter of distilled water with agitation. After one hour of settling for water absorption, the water-polymer was filtered through a 100 mesh sieve and the amount of water absorbed determined by measuring the volume of filtrate recovered. In addition, parallelly, 5 gr. of the polymers of Examples 1-7 were added to 1 liter of 1 percent NaCl solution, and testing was conducted the same as in the case of distilled water. The results of the testing are shown in Table I. Water absorbability is shown as amount of absorbed water/weight of resin.

Although any alkaline metal and any amine can be used for neutralization of the acrylic acid, the ammonium acrylate has been found to have the best solubility in water so that a higher concentration of the ammonium acrylate salt in water is possible. Further, the polymer manufactured with the ammonium acrylate salt is superior in water absorption. Further, it has been found that the incorporation of acrylamide in the polymerization process provides a polymer having better solubility in water and better stability in the manufacturing process.

TABLE I

| | Examples 1-7 | |
|---|---|---|
| - | Distilled Water | 1% NaCl Solution |
| Example 1 | 650 times | 68 times |
| Example 2 | 670 times | 70 times |
| Example 3 | 680 times | 72 times |
| Example 4 | 620 times | 65 times |
| Example 5 | 540 times | 57 times |
| Example 6 | 520 times | 54 times |
| Example 7 | 540 times | 56 times |
| Commercial product (1) | 520 times | 49 times |
| Commercial product (2) | 504 times | 47 times |

EXAMPLE 8

52.7 gr. of acrylic acid and 17.3 gr. of acrylamide were dissolved in 20 gr. of distilled water 32.8 gr. of KOH was added for 80 mole percent partial neutralization of acrylic acid. Then 0.007 gr. of N,N'-methylenebisacrylamide polyvinyl monomer was added with 2.5 gr. of methylcellulose. The aqueous monomer mixture was homogenized with agitation. Next, as an initiator, 0.7 gr. of 2,2'-azobisisobutyronitrile dissolved in 10 cc of acetone was added. This mixed solution was kept at 80° C. in a water bath surrounding the reaction chamber. Polymerization was initiated as the temperature of the mixture increased as a result of the surrounding water bath, resulting in a white, solid porous resin.

EXAMPLE 9

20.8 gr. of acrylamide was dissolved in 49.2 gr. of acrylic acid and 28.0 gr. of aqueous ammonia (29% concentration) was added for 70 mole percent neutralization of the acrylic acid. Next, 0.01 gr. of N,N'-methylenebisacrylamide and 5 gr. of methylcellulose were added and stirred to homogenize. As an initiator, 0.7 gr. of 2,2'-azobis(2-amidinopropane)-hydrochloride dissolved in 5 gr. of distilled water, was added. The polymerization was initiated in a TEFLON coated glass reaction chamber kept at 80° C., as in Example 8 yielding a white, solid porous resin having a water content of about 10% by weight.

EXAMPLE 10

70 gr. of acrylic acid was dissolved in 20 gr. of distilled water. 40.8 gr. of KOH was added to neutralize 75 mole percent of the acrylic acid. Next, 0.007 gr. of N,N'-methylenebisacrylamide and 2.0 gr. of methylcellulose were added, and the mixture homogenized with agitation. Then, as an initiator, 0.7 gr. of 2,2'-azobisisobutyronitrile dissolved in 10 cc. of acetone was added. This solution was transferred to the reaction chamber kept at 80° C. and polymerization was initiated with a rise in temperature of the mixture resulting in a white, solid porous resin of low water content.

EXAMPLE 11

Same as Example No. 8, but having no methylcellulose.

EXAMPLE 12

Same as Example No. 9, but having no methylcellulose.

EXAMPLE 13

Same as Example No. 10, but having no methylcellulose.

The water absorbable resins of Example 8-13 were pulverized directly into powder without any drying process.

The water absorbing capacity of the resins of Examples 8-13 was tested as follows:

1 gr. of the resin powders (20-40 mesh) of Examples 8-13 were each added to 2 liters of distileld water with agitation. After settling for 1 hour, the water-polymers were filtered through a 100 mesh sieve and the volume of filtrate measured to give the amount of water absorbed in the resin. In addition, 5 gr. of the resins of Examples 8-13 were each added to 1 liter of 1% NaCl solution, and the testing was conducted the same as the case of distilled water. The results are shown in Table II. Water absorbability is shown as amount of absorbed water/weight of resin

TABLE II

| | Examples 8-13 | |
|---|---|---|
| | Distilled Water | 1% NaCl Solution |
| Example 8 | 1,300 times | 98 times |
| Example 9 | 1,160 times | 84 times |
| Example 10 | 1,360 times | 102 times |
| Example 11 | 540 times | 56 times |
| Example 12 | 470 times | 50 times |
| Example 13 | 590 times | 60 times |

EXAMPLE 14

52.7 gr. of acrylic acid and 17.3 gr. of acrylamide were dissolved in 20 gr. of distilled water. 32.8 gr. of potassium hydroxide was added to neutralize 80 mole percent of the acrylic acid. Next, 0.007 gr. of N,N'-methylenebisacrylamide and 5 gr. of a polystyrene emulsion were added and homogenized under stirring. The polystyrene emulsion had a concentration of 50 weight percent and a polystyrene grain size of abouit 0.5 micro meters. Then, as the initiator, 0.7 gr. of 2,2'-azobisisobutyronitrile dissolved in 10 cc. of acetone solution was added. The mixed monomer solution was kept at 80° C. in the reaction chamber immersed in a water bath. With the increasing temperature of the mixed monomer solution polymerization was initiated resulting in a white, solid, porous resin.

EXAMPLE 15

20.8 gr. of acrylamide was dissolved in 49.2 gr. of acrylic acid. 28.0 gr. of aqueous ammonia (29% concentration) was added to neutralize 70 mole percent of the acrylic acid. Then 0.01 gr. of N,N'-methylenebisacrylamide was added. 3 gr. of the polystyrene emulsion of Example 14, but having a 1 micro meter average grain size, was added and the mixed solution was homogenized with agitation. Next, as the initiator, 0.7 gr. of 2,2'-azobis(2-amidinopropane)-hydrochloride dissolved in 5 gr. of distilled water was added. The solution was kept at 80° C. as in Example 14 and polymerization was initiated with increased temperature resulting in a white, solid, porous resin.

EXAMPLE 16

70 gr. of acrylic acid was dissolved in 20 gr. of distilled water and 40.8 gr. of KOH was added to neutralize 75 mole % of the acrylic acid. Next, 0.007 gr. of N,N'-methylenebisacrylamide was added. 2 gr. of the polystyrene emulsion of Example 14 (but having an average grain size of 5 micro meters), was added and the mixture homogenized. Next, as the initiator, 0.7 gr. of 2,2'-azobisisobutyronitrile dissolved in 10 cc. of acetone was added. The mixed solution was kept at 80° C. in the water bath to initiate the polymerization resulting in a white, solid, porous resin.

EXAMPLE 17

Same as Example 14, but having no polystyrene.

EXAMPLE 18

Same as Example 15, but having no polystyrene.

EXAMPLE 19

Same as Example 16, but having no polystyrene.

The polymers of Examples 14–19 were made into powdery resins without any drying step.

The following tests were performed on the resins of Examples 14–19 to determine water absorbing capacity: 1 gr. of the resins of Examples 14–19 (20–40 mesh) were each added into 2 liter of distilled water with agitation and settling for one hour. After settling, a 100 mesh sieve was employed for filtration and the amount of absorbed water was calculated from the amount of filtrate. Their water absorption rate (absorbed water/weight of polymer) is shown in the following Table III.

TABLE III

| | Examples 14–19 | |
|---|---|---|
| | Distilled Water | 1% NaCl Solution |
| Example 14 | 1,010 times | 83 times |
| Example 15 | 960 times | 76 times |
| Example 16 | 1,120 times | 90 times |
| Example 17 | 540 times | 56 times |
| Example 18 | 470 times | 50 times |
| Example 19 | 590 times | 60 times |

We claim:

1. A method of manufacturing a composition comprising mixing a monomer solution of (A) acrylic acid, neutralized 70 to 100 mole percent, (B) acrylamide in a mole ratio of (A):(B) in the range of 70:30 to 100:0; (C) a water soluble or water miscible polyvinyl monomer cross-linking agent in an amount of 0.001 to 0.3 percent by weight of (A) plus (B); and water to form a mixed monomer solution, wherein the monomers of the mixed monomer solution consist essentially of (A), (B) and (C) and the monomer concentration is at least 70 percent by weight of the monomer solution prior to polymerization initiation; adding polystyrene to said mixed monomer solution having a grain size less than or equal to 5 micrometers in an amount of 0.5 to 10 percent based on the total weight of monomers in the mixed monomer solution; and initiating polymerization of monomers (A) and (B) such that during polymerization, the exothermic heat of reaction is substantially the only heat energy used to accomplish polymerization, cross-linking and to drive off sufficient water to form a water absorbing cross-linked resin composition having a water content of 15 percent by weight or less.

2. A method of manufacturing a composition comprising mixing a monomer solution of (A) acrylic acid, neutralized 70 to 100 mole percent, (B) acrylamide in a mole ratio of (A):(B) in the range of 70:30 to 100:0; (C) a water soluble or water miscible polyvinyl monomer cross-linking agent in an amount of 0.001 to 0.3 percent by weight of (A) plus (B); and water to form a mixed monomer solution, wherein the monomers of the mixed monomer solution consist essentially of (A), (B) and (C) and the monomer concentration is at least 70 percent by weight of the monomer solution prior to polymerization initiation; adding methylcellulose to said mixed monomer solution having a grain size less than or equal to 5 micrometers in an amount of 0.5 to 10 percent based on the total weight of monomers in the mixed monomer solution; and initiating polymerization of monomers (A) and (B) such that during polymerization, the exothermic heat of reaction is substantially the only heat energy used to accomplish polymerization, cross-linking and to drive off sufficient water to form a water absorbing cross-linked polyacrylate resin composition having a water content of 15 percent by weight or less.

3. A method of manufacturing a composition comprising mixing a monomer solution of (A) acrylic acid, neutralized 70 to 100 mole percent, (B) acrylamide in a mole ratio of (A):(B) in the range of 70:30 to 100:0; (C) a water soluble or water miscible polyvinyl monomer cross-linking agent in an amount of 0.001 to 0.3 percent by weight of (A) plus (B); and water to form a mixed monomer solution, wherein the monomers of the mixed monomer solution consist essentially of (A), (B) and (C) and the monomer concentration is at least 70 percent by weight of the monomer solution prior to polymerization initiation; incorporating a porosity increasing agent into said mixed monomer solution selected from the group consisting of polystyrene and methylcellulose in an amount of 0.5 to 10 percent based on the total weight of monomers in the mixed monomer solution; and initiating polymerization of monomers (A) and (B) such that during polymerization, the exothermic heat of reaction is substantially the only heat energy used to accomplish polymerization, cross-linking and to drive off sufficient water to form a water absorbing cross-linked polyacrylate resin composition having a water content of 15 percent by weight or less, and wherein said neutralized acrylic acid is one other than potassium acrylate.

* * * * *